United States Patent
Fry

Patent Number: 6,148,262
Date of Patent: *Nov. 14, 2000

[54] SPORTS COMPUTER WITH GPS RECEIVER AND PERFORMANCE TRACKING CAPABILITIES

[76] Inventor: William R. Fry, 605 Echoglun Ct., Colorado Springs, Colo. 80906

[*] Notice: This patent is subject to a terminal disclaimer.

[21] Appl. No.: 09/459,736

[22] Filed: Dec. 13, 1999

Related U.S. Application Data

[63] Continuation of application No. 08/742,373, Nov. 1, 1996, Pat. No. 6,002,982.

[51] Int. Cl.[7] .................................................. G06F 165/00
[52] U.S. Cl. ......................... 701/213; 701/211; 701/214; 340/427; 340/432; 482/57
[58] Field of Search ..................................... 701/200, 201, 701/207, 208, 209, 211, 213, 214, 216; 340/427, 432; 482/57

[56] References Cited

U.S. PATENT DOCUMENTS

| | | | |
|---|---|---|---|
| 4,163,216 | 7/1979 | Arpino | 340/870.13 |
| 4,642,606 | 2/1987 | Tsuyama | 324/174 |
| 4,862,395 | 8/1989 | Fey et al. | 364/561 |
| 5,008,647 | 4/1991 | Brunt et al. | 324/168 |
| 5,119,101 | 6/1992 | Barnard | 342/357 |
| 5,148,002 | 9/1992 | Kuo et al. | 219/211 |
| 5,191,792 | 3/1993 | Gloor | 73/178 R |
| 5,210,540 | 5/1993 | Masumoto | 701/213 |
| 5,335,188 | 8/1994 | Brisson | 364/551.01 |
| 5,420,592 | 5/1995 | Johnson | 342/357 |
| 5,506,774 | 4/1996 | Nobe et al. | 701/213 |
| 5,552,794 | 9/1996 | Colley et al. | 342/357 |
| 5,592,401 | 1/1997 | Kramer | 364/550 |
| 5,629,668 | 5/1997 | Downs | 340/427 |
| 5,757,929 | 5/1998 | Wang et al. | 381/24 |
| 5,815,126 | 9/1998 | Fan et al. | 345/8 |
| 5,825,327 | 10/1998 | Krasner | 342/357 |
| 5,862,511 | 1/1999 | Croyle et al. | 701/213 |

*Primary Examiner*—William A. Cuchlinski, Jr.
*Assistant Examiner*—Gertrude Arthur
*Attorney, Agent, or Firm*—Gifford, Krass, Groh, Sprinkle, Anderson & Citkowski, PC

[57] ABSTRACT

A sports computer having an integral global satellite positioning (GPS) receiver and computer interfacing capability enables functional and/or performance characteristics to be tracked and analyzed as a function of geographical position and/or elevation. The computer includes mounting means and/or interfaces to one or more sensors to measure operational and/or physiological parameters such as heart rate, or weather conditions such as temperature. Means are provided for downloading the stored geographical and sensor parameters to an external personal computer so that the data collected during a workout may be reviewed and analyzed on the screen of the PC. Preferably, map data may also be stored enabling the collected data to be viewed relative to the map information, for example, in superposition.

6 Claims, 3 Drawing Sheets

SPORTS COMPUTER WITH GPS RECEIVER AND PERFORMANCE TRACKING CAPABILITIES

REFERENCE TO RELATED APPLICATION

This application is a continuation of U.S. patent application Ser. No. 08/742,373, filed Nov. 1, 1996, now U.S. Pat. No. 6,002,982, the entire contents of which is incorporated herein by reference.

FIELD OF THE INVENTION

The present invention relates generally to computer-based systems of the type which display speed, used for sports training purposes, and, more particularly, to a system including a GPS receiver and means for transferring measurements to a personal computer to facilitate the tracking and mapping of route and athlete performance parameters.

BACKGROUND OF THE INVENTION

Sports-related measurement systems have grown dramatically in sophistication, over the years. With respect to bicycling, such systems have evolved from older, heavy speedometers, and the like, to modern electronic units capable of monitoring and displaying a number of performance characteristics.

So-called bicycle computers, which for example, track and electronically display speed, distance, and so forth, are now common in the art. The following examples are illustrative of known systems of this type. In U.S. Pat. No. 4,642,606, entitled "DATA DISPLAY UNIT FOR A BICYCLE" to Tsuyama, there is disclosed a handlebar-mounted display unit to which a wheel and crank sensor are communicatively interfaced, affording the calculation of running data such as speed, distance, average speed, maximum speed and so forth, based upon electrical pulses received from the wheel and crank sensors. U.S. Pat. No. 4,862,395 entitled "DATA DISPLAY INSTRUMENT FOR A BICYCLE" to Fey et al. includes most of the same features of the device of Tsuyama, but claims to improve upon the display by providing an analog scale field to display traveling speed and pedaling speed on a momentary, more readable basis. The '395 patent also includes a sensor associated with wheel rotation, and an additional sensor associated with pedal speed to determine cadence. In addition to the devices just described, others exist, both in patent literature and as commercially available products.

Bicycle computers also exist which have output ports enabling the device to be interfaced to a commercially available personal computer. The invention, "BICYCLE COMPUTER WITH MEMORY AND MEANS FOR COMPARING PRESENT AND PAST PERFORMANCE IN REAL TIME," disclosed in U.S. Pat. No. 5,335,188 to Brisson, for example, discloses a device for monitoring and comparing present, past and ideal performance on an exercise machine such as a bicycle. The system operates under a predetermined set of user-controlled instructions, to store a set of performance data in memory, which can then be compared against a stored, user selected performance data. Comparisons among these various data sets may then be displayed.

The exercise computer of Brisson includes a connector (65) for linking to an external computer, but the capabilities involved are extremely limited. In one example given, data in the memory of the computer itself may be transmitted to the external computer for "safekeeping," then transferred back to the cycle computer at a later time. The specified purpose is to ensure that the data are not lost should the memory suffer from a power failure, should the cycle computer be stolen. Alternatively, if the user rides on many different routes, the cycle computer may not have enough memory to save all ride data, in which case the connector (65) may be used to transfer a larger number of pace files to an external computer such as a PC. Thus, according to the '188 patent, although a computer interface is provided, it is essentially limited in function to that of a memory expansion port.

Despite the various speed, distance and cadence functions available through existing cycle-mounted computers, none receive geographical coordinates through, for example, a global positioning satellite (GPS) receiver. Although a variety of vehicle-oriented tracking and mapping systems do exist which include GPS capabilities, none exist for bicycles. However, the inclusion of such a capability within a bicycle computer provides a number of unique advantages, as will be explained in the sections herein detailing the instant invention. As one such advantage, by utilizing an additional satellite to obtain altitude as well as longitude/latitude coordinates, the cyclist may be provided with elevation as well as geographic location information, which may be particularly useful in determining performance, endurance, and other characteristics. Moreover, by obtaining and storing position and/or altitude information, these characteristics may be tracked in terms of location and/or altitude, enabling the cyclist to visualize speed, cadence and other external and/or physiological characteristics as a function of geographical position, further allowing performance attributes to be tracked and plotted, for example, on an external personal computer. By combining GPS capabilities with the various functional and performance monitoring and tracking capabilities disclosed herein, the rider may not only visualize performance as a function of geometry, including incline, but will also be more equipped to optimize performance, by determining when cadence, gearshifting, and other riding changes were, or should have been, executed.

SUMMARY OF THE INVENTION

The present invention improves upon the prior art by providing a sports computer having an integral global satellite positioning (GPS) receiver and computer interfacing capability, enabling functional and/or performance characteristics to be tracked and analyzed as a function of geographical position and/or elevation. Though the descriptions herein focus on a bicycling implementation, the invention is readily applicable to other sports involving travel over time, regardless of the equipment involved, including running, rowing, kayaking, gliding, etc. In a cycling application, for example, in addition to sensors for vehicle speed and cadence, the invention further includes, in alternative embodiments, sensors for heart rate, and weather conditions such as temperature and wind speed/direction.

In a preferred embodiment, the device according to the invention includes means for mounting an enclosed mobile computer system directly to the athlete or equipment in use, with interfaces to one or more sensors which measure performance characteristics. A GPS receiver and small antenna are also included within and on the device, enabling the geographical information to be gathered and stored therein. Preferably the receiver communicates with sufficient satellites to determine altitude information as well as longitudinal and latitudinal coordinates. The device according to the invention includes sufficient memory to store geographical coordinates on a periodic basis, even for a long-term use, which may constitute several days.

Also in a preferred embodiment, the inventive device is capable of being interfaced to an external computer such as a personal computer (PC), including a laptop computer, so that the data collected during a workout may be reviewed and analyzed on the screen of the PC. Preferably, map data may also be stored, either in the mobile aspect of the invention or, more conveniently, within the PC on CD-ROM, enabling the collected data to be viewed relative to the map information, for example, in superposition with respect thereto.

In addition to the inclusion of a GPS receiver capability, in alternative embodiments, the invention may optionally include a heart-rate sensor, preferably in the form of a check or appendage pressure sensor, as well as weather condition sensors to provide temperature and/or wind speed/direction indications. Such parameters, if collected, are also stored along with, and in conjunction with, the GPS information for later review on the personal computer. The mobile aspect may either be left on the equipment used by the athlete, with the collected data being removed on a computer-accessible module or card containing a non-volatile memory in some form, whether inherently or through battery back-up. As an alternative, the mobile unit may be disconnected from its sensor inputs and removed for relocation proximate to the PC, with the data being accessed through a connector joining the PC to the mobile unit.

DETAILED DESCRIPTION OF THE PREFERRED EMBODIMENT

Figure 1:
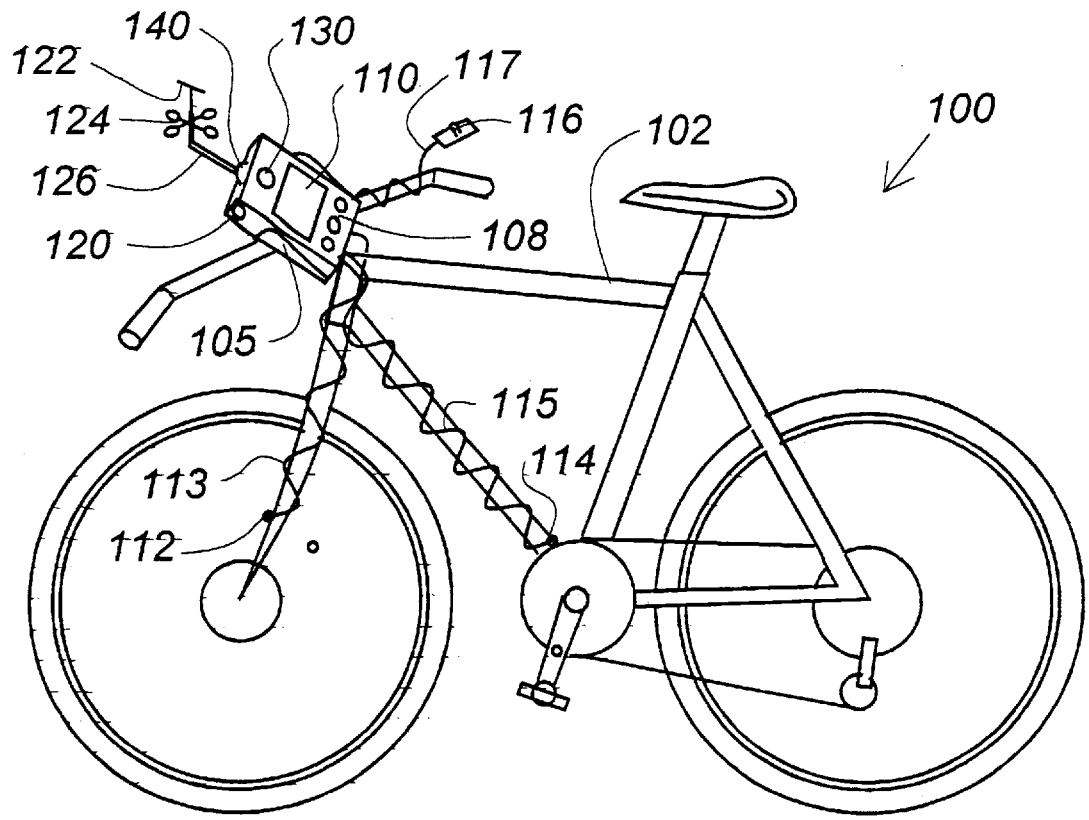
FIG. 1 is an oblique drawing of a sports computer according to the invention for cycling use, including a GPS receiver and a comprehensive complement of other functional, physiological and external condition sensors.

Reference will now to be made to the accompanying figures, wherein like reference numerals refer to like elements, though such elements may be present in more than one drawing. FIG. 1 illustrates, from an oblique perspective at 100, a bicycle 102 having mounted thereon a bicycle computer 104 according to the invention. With the exception of sensors and associated hardware, the electrical subsystems are contained within an enclosure mountable on the bicycle 102, preferably in the form of a cradle 106 within which the enclosure 104 is releasably held for mobile use, yet enabling the enclosure to be detached therefrom for computer interfacing, as best understood with reference to FIG. 4.

On the enclosure 104 there is supported an operator control including a set of mode switches 108 and a display 110, preferably based upon low-power liquid-crystal display (LCD) technology. Various sensors are interfaced to the computer contained within the enclosure 104, preferably through a connector common to all such connections, enabling the enclosure 104 to be most conveniently detached and removed from the cradle 105 for the downloading of the data collected during a particular ride. At the very least, the system includes a speed sensor 112 attached to the computer electronics via cable 113, which attaches to a connector point on the enclosure 104 (not visible in the drawing). In the preferred embodiment, a crank speed sensor 114 is also included, this being connectable to the computer electronics via cable 115. Although different sensing technologies may be used, this invention preferably uses moving magnets which induce a signal into a stationary sensor mounted appropriately on the bike frame containing a lead switch as in the '606 patent to Tsuyama, or, more preferably, a Hall-effect sensor. With sensors 112 and 114 for wheel speed and crank speed, respectively, various aspects may be monitored or computed, including speed, cadence, distance traveled, and time/distance remaining if terminal trip parameters are entered. Additionally, with wheel rotation and crank rotation being known, gear ratio may also be computed, that is, the gear settings used by the rider at that point in time. As an alternative to the use of a discrete crank sensor, according to the invention, since the system is capable of determining ground speed and gear ratio, pedal revolutions per minute may be calculated. An additional sensor may be used to sense what gear the bike is in, with the software preferably allowing for the ability to input or change gear set, as serious riders typically have more than one set. In addition to speed and cadence sensing, a heart rate monitor may be included, preferably in the form of a chest or appendage pressure sensor or, alternatively, in the form of a finger cot 116, facilitating a very short connection 117 to be made to the enclosure 104.

In addition to sensors which measure cycle functional or operational characteristics and rider physiology, additional sensors may be provided according to the invention to determine weather conditions. In particular, a temperature sensor 120 may be mounted on an outer surface of the enclosure 104, preferably with appropriate wind shielding to guard against false readings. Additionally, an optional wind sensing apparatus including a wind direction indicator 122 and wind speed monitor 124 may be provided on a mount 126, either emanating from the enclosure 104 or mounted elsewhere on the bike, preferably away from the rider, again, so that the existing wind pattern is not disturbed. Although, obviously, as the bike travels at high speed in a particular direction, accurate indications of wind direction and speed would not be possible. However, since, for reasons explained below, the rider's direction and speed may be known or computed, the effects of bicycle movement may be subtracted from those of the indicators 122 and 124 to obtain wind-related readings which at least approximate existing weather conditions. In addition to the various sensors just described, others may be provided internal to the enclosure 104, and therefore not visible, such as an electronic compass which, as described above, may be interfaced to the wind detection sensors to subtract bicycle movement effects for a more accurate reading.

Figure 2:
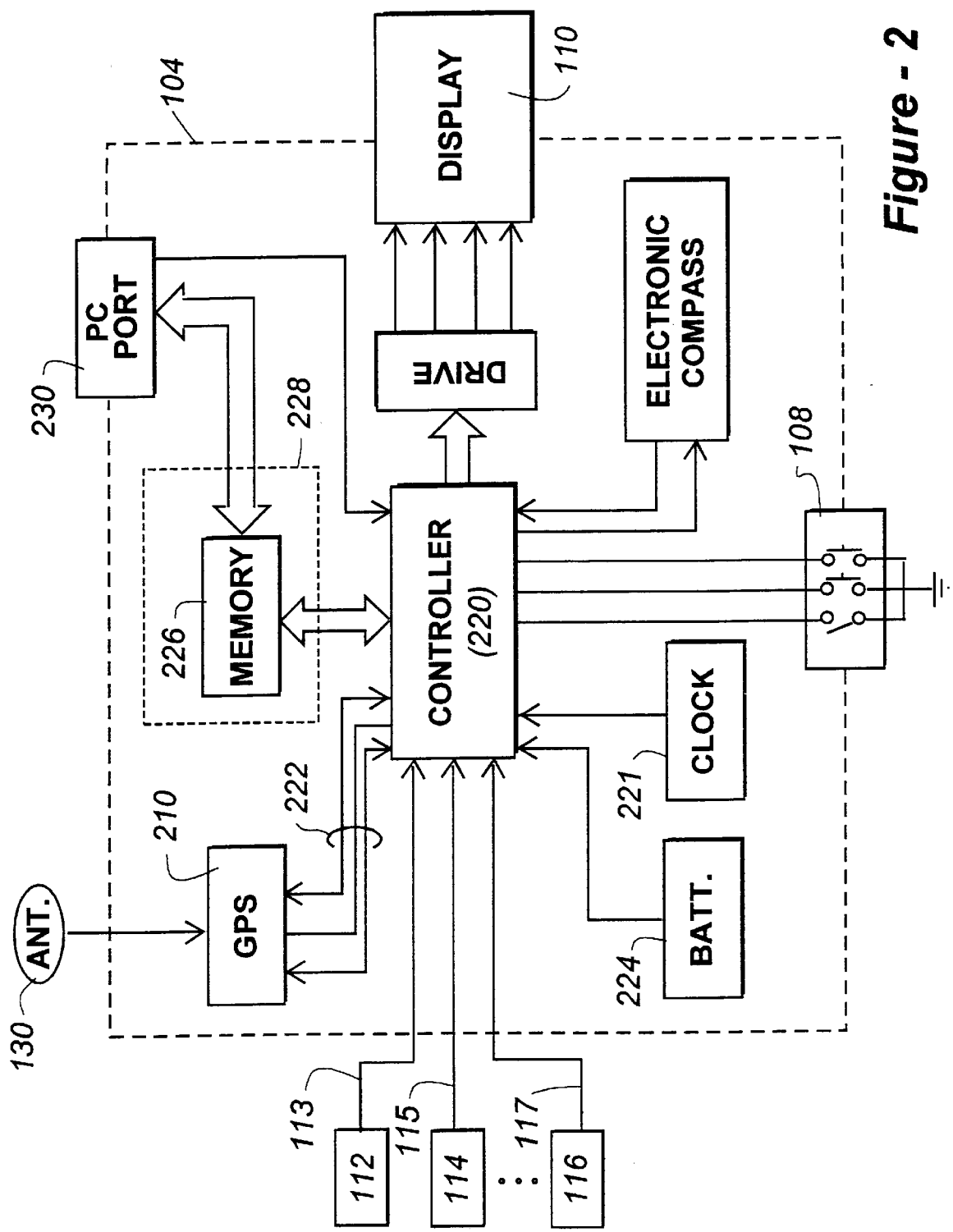
FIG. 2 is a block diagram of a sports computer according to the invention, including major electrical subsystems and connections therebetween.

Continuing the discussion of FIG. 1, also supported on the enclosure 104 is a global positioning satellite (GPS) antenna which interfaces to a GPS receiver, the functioning of which is better understood with reference to FIG. 2. The antenna 130 interfaces to a GPS receiver 210 which connects to central controller 220 via signal lines 222. Although the receiver 210 may be constructed from discrete components, in the preferred embodiment, the receiver 210 is implemented using a "signal-chip" GPS receiver which have recently become commercially available from various manufacturers. Signal lines 222 include power-up/satellite locating signals from the processor 220, as well as positional information which is delivered to the processor 220 via an interrupt structure, better understood with reference to the flowchart and text accompanying of FIG. 3. The controller 220 is preferably a single-chip microcomputer of conventional design, implemented using C-MOS technology to consume the least amount of power during use, which is provided in the preferred embodiment through a rechargeable battery pack 224. Timing for the microcomputer controller 220 is preferably provided by a crystal-controlled clock 221. Though not shown in the figures, optional solar cells may also be used as a primary power source or to charge the batteries 224 during use.

Also interfaced to controller 220 is a memory 226 into which geographical information received from the GPS receiver electronics 210 is stored, along with information received and decoded, if necessary, from the various sensors, depending upon the overall configuration. In the preferred embodiment, the memory 226 uses one or more C-MOS random-access memories, again, to conserve power. The memory 226 may either be removable on a board or card 228 and transferred to a personal computer for downloading in that manner, thus requiring that the memory 226 be rendered non-volatile, either inherently, as in the form of an electrically erasable programmable read-only memory (EEPROM), for example, or through the use of a battery (not shown) for back-up purposes.

As an alternative to this means for transferring collected ride data to a personal computer, such information may be downloaded through PC port 230, in which case the entire cycle computer enclosure 104 would be removed from its carrying mechanism and placed proximate to the personal computer for access thereby, as best seen and described with reference to FIG. 4.

Figure 3:
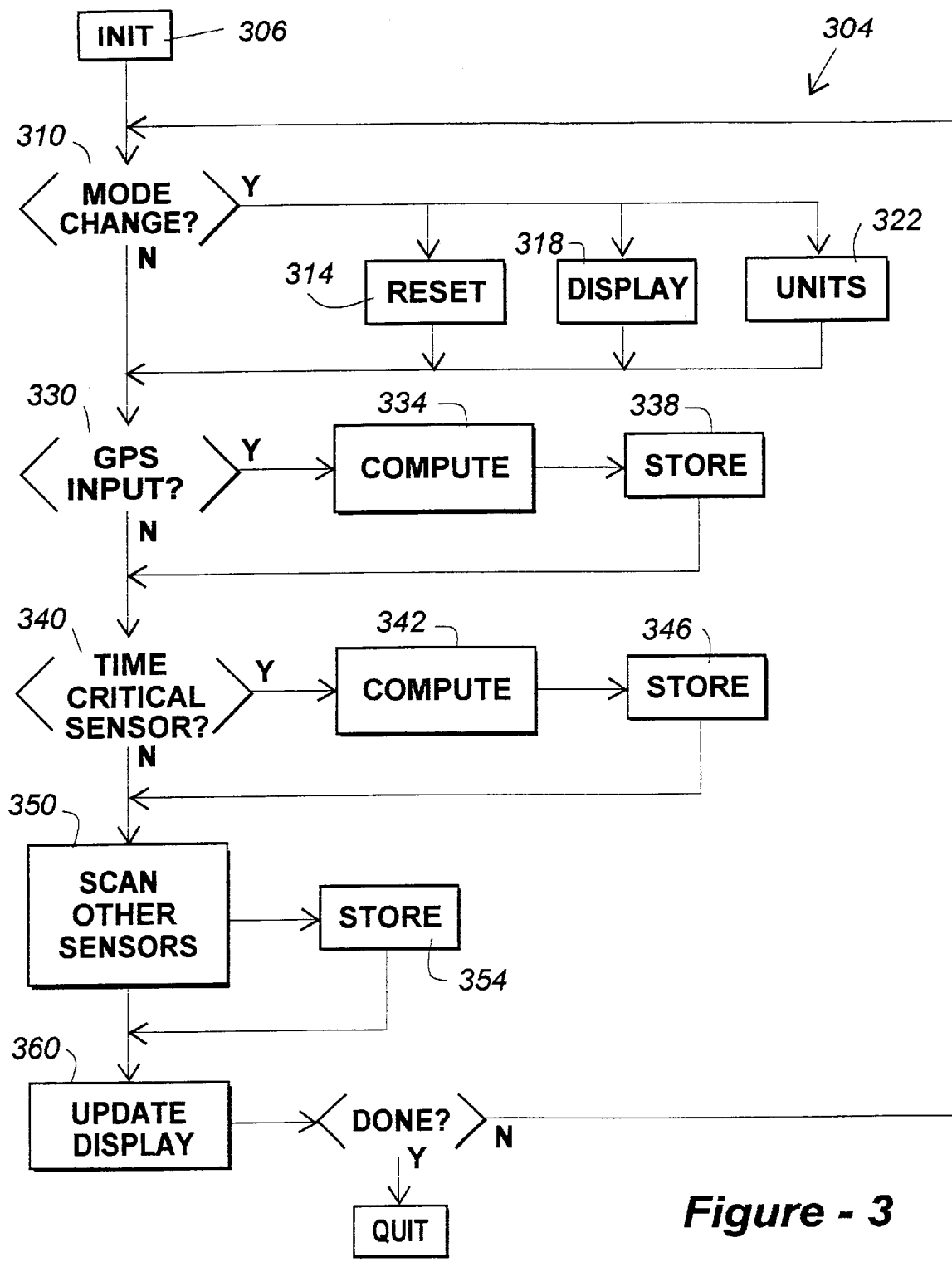
FIG. 3 is a flowchart used to indicate major subroutines and other operations performed by a software aspect of the invention.

Now making reference to FIG. 3, there is shown generally at 304 a flowchart representative of major software routines executed by controller 220 contained within the enclosure 104 of a bicycle computer according to the invention. Although FIG. 3 does not provide a functional block for all steps executed by the computer, the following description will enable one of ordinary skill in the art of microcomputer programming to write code for all of the routines involved. Upon power-up, the controller executes an initialization routine identified at block 306, wherein, in particular, the GPS receiver 210 cycles through its satellite-finding routine, a requirement to all such GPS subsystems. Also at this stage, the controller may test to see which sensors are connected, as well as perform other input/output (I/O), memory-management functions, and so forth.

Next, at block 310, the controller scans the mode switches 108 to determine if a change in desired functionality has occurred. At block 314, for example, the controller checks to see if the system has been reset, in which case the contents of memory 226 may be cleared on a global or selective basis, preferably in accordance with operator responses to queries presented on the display 110. If there has been a change in display mode, as signified with block 318, appropriate parameters will be loaded so that, at the execution of the update display block 360 as described below, the parameters desired by the operator will be displayed, be they geographic position, speed or physiological or weather conditions, or any combination thereof, depending upon configuration. As a further option, at block 322, another one of the switches 108 may be chosen so that distance and speed read-out may be in English or metric, in accordance with the operator's preference. It should be clear that, in accordance with available hardware options, additional mode-related commands may be executed in response to an affirmative answer to the question at block 310.

Having attended to mode-related functions, the controller next executes the most time-critical routines, preferably in the form of interrupts, followed by a scanning of less-time critical sensor inputs, after which the display is updated in accordance with new and previously stored parameters. More particularly, at block 330, if, through a mode selection, a GPS position is to be received, an interrupt is generated, and the new coordinates are computed at block 334 and stored in memory at block 338. Although updating the GPS coordinates may take place on a non-interrupt basis, the received coordinates would have to be maintained in a buffer until servicing, potentially adding additional, unnecessary hardware.

Next, in a preferred embodiment, the controller next inputs signals received from time-based sensors, if updates are warranted in response to block 340. If so, such inputs, which include vehicle speed, crank rate, the cyclist's heart rate, and so forth are decoded at block 342 and stored in memory of block 346. Again, these being time-based inputs, they are preferably received in the form of an interrupt to avoid unnecessary buffering. Although, in certain cases, one or more of these signals may be missed, for example, in the event of a contemporaneously received GPS input, the system can easily extrapolate through the missing inputs and catch up on an accurate rate and readout, and store information representative of the missed signals in the memory for later display and analysis on the personal computer.

At block 350, less time-critical sensors are simply scanned by the controller. These include internal electronic compass heading, weather sensors and so forth, which do not change on a time-critical or even periodic basis. Thus, in these cases, the sensors are simply scanned after time-critical interrupts are first serviced. At block 360, the least critical function takes place, that is, the display is updated by refreshing from memory the data to be displayed in accordance with the mode selected. In other words, a portion of the memory 226 may be set aside and utilized as a buffer for the display 110. After updating the display at block 360, the software loops back to the mode-selection inquiry at block 310, and the various routines are repeated, or skipped, in accordance with mode and the existence of various inputs.

Figure 4:
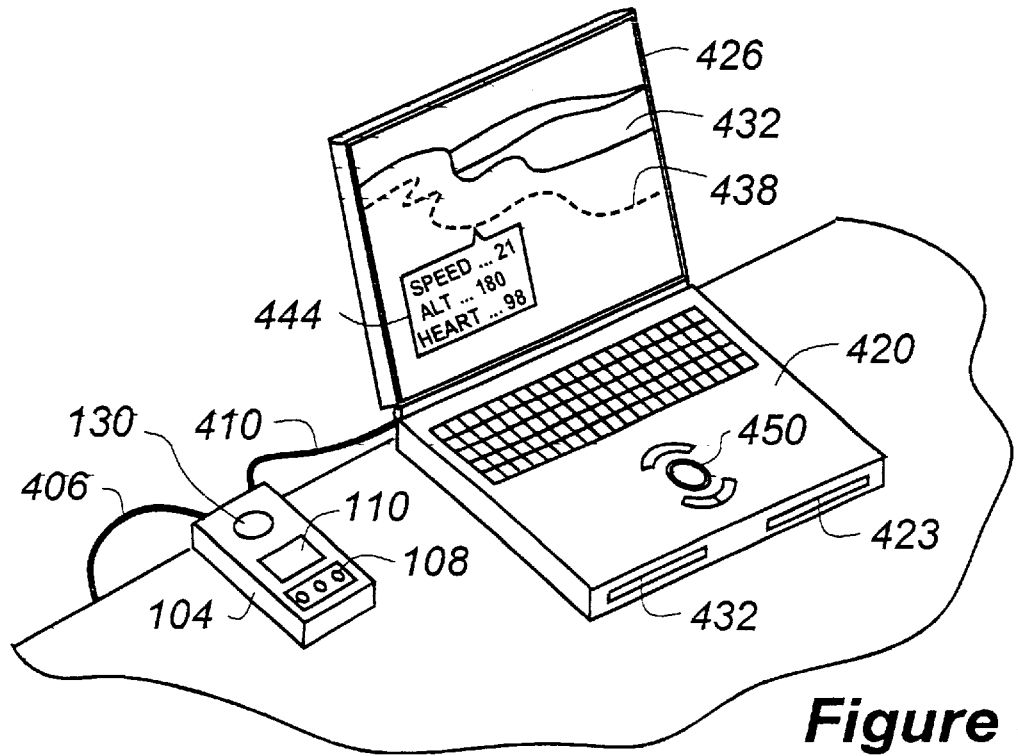
FIG. 4 is a drawing as seen from an oblique perspective which shows a sports computer according to the invention removed from its mobile mounted state and connected to a personal computer to view route information and performance characteristics through pull-down menus associated with various points along a particular workout route.

Now making reference to FIG. 4, there is shown generally at 402, the situation wherein the computer 104 has been removed from its holster 105 and connected to a personal computer 420 through an interface cable 410 designed for this purpose. Another cable, 406, is preferably interfaced to the computer 104 to provide power during the downloading process which will now be described, and to recharge the batteries internal to the unit 104. As mentioned, although in the following discussion the entire computer 104 has been removed in interface to the personal computer 420, in an alternative embodiment, the unit 104 may remain attached to the bicycle, with a card being removed therefrom having ride parameters stored thereon, inserted into or in some way interfaced to the personal computer 420. As just one example, the so-called PCM CIA cards may be utilized for such a purpose.

In any event, with the contents of the computer 104 being interfaced to the personal computer 420, an application program according to the invention may be loaded into the computer 420, through a diskette port 423, for example, enabling the route taken by a particular ride to be displayed as a plot 438, preferably superimposed over a map 432 on the display 426 of the PC 420. Although the invention may be used without such map data, for example, by simply listing ride characteristics as a function of geographical positioning, the inclusion of maps for superposition of the ride and characteristics as described below, provides for a much more exciting and user-friendly interface. Such map data are becoming increasingly available for a variety of useful applications, and may conveniently be input to the system via CD-ROM port 432, containing the appropriate map data.

Although ride characteristics may be displayed in a number of ways, in the preferred embodiment, pop-up menus 444 appear in response to an operator clicking with a pointing device 450 on a point of the path 438. Preferably, such menus 444 contain the information present at that point along the ride, including detailed geographical information, along with altitude, plus any other bicycle operation, cyclist physiological or external condition sensing that took place at that point or the point closest to that selected by the user.

As an alternative to the map-based display shown on the display screen in FIG. 4, if altitude information is available, it may be more elucidating to plot altitude along with other ride characteristics, particularly if the cyclist is more interested in improving his or her technique than seeing where they went. In other words, by plotting altitude and connecting the various points to show ride incline, and by plotting in a concurrent, synchronized manner the cyclist's heart rate, speed, gear ratio, and so forth, it may be easy to see how hard the cyclist was working as a function of incline, when and if the correct gears were being used, and so forth. It will be apparent to one of skill that other display modes are also possible according to the invention.

What is claimed is:

1. A sports activity monitoring system, comprising:

a) a portable recording unit adapted to travel with a user while engaged in a sports activity within a geographical area, the portable unit including:
      a global positioning (GPS) satellite receiver,
      a memory, and
      the first portion of a computer interface,
      the portable unit being operative to perform the following functions:
         receive a signal from the GPS receiver relating to the geographic position of the user while engaged in the sports activity, and
         store the geographic position information in the memory; and b) a computer, including:
      a memory for storing a map of the geographical area, and
      the second portion of the computer interface,
      the computer being operative to perform the following functions in conjunction with the portable unit:
         receive the geographic position information from the portable unit through the computer interface, and
         display the route taken by the user while engaged in the sports activity in superposition with the map of the geographical area.

2. The system of claim 1, wherein the computer is further operative to display the speed of the user while engaged in the sports activity.

3. The system of claim 1, wherein the signal from the GPS receiver includes altitude information, enabling the computer to display the altitude of the user while engaged in the sports activity.

4. A method of analyzing a route taken by an individual engaged in an outdoor activity within a geographical area, comprising the steps of:

storing a map of the geographical area in a computer interfaced to a display device;

providing the individual with a portable recording unit containing a global positioning (GPS) satellite receiver;

recording the location of the individual during the activity;

upon completion of the route, downloading the location of the individual to a computer; and displaying, on the display device of the computer, the location of the user on the map.

5. The method of claim 4, further including the step of displaying the speed of the user while engaged in the outdoor activity.

6. The method of claim 4, further including the step of displaying the altitude of the user while engaged in the outdoor activity.

* * * * *